(12) United States Patent
Abrecht et al.

(10) Patent No.: US 6,403,824 B2
(45) Date of Patent: Jun. 11, 2002

(54) PROCESS FOR THE PREPARATION FOR 4, 5-DIAMINO SHIKIMIC ACID DERIVATIVES

(75) Inventors: Stefan Abrecht, Duggingen; Martin Karpf, Reinach; René Trussardi, Birsfelden; Beat Wirz, Reinach, all of (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/777,277

(22) Filed: Feb. 6, 2001

(51) Int. Cl.⁷ .............................................. C07C 205/00
(52) U.S. Cl. ..................... 560/125; 548/961; 549/463; 549/465
(58) Field of Search .......................... 560/125; 549/463, 549/465; 548/961

(56) References Cited

FOREIGN PATENT DOCUMENTS

| WO | WO 98/07685 | 2/1998 |
|----|-------------|--------|
| WO | WO 99/14185 | 3/1999 |
| WO | WO 01/28981 | 4/2001 |

OTHER PUBLICATIONS

Rohloff et al., J. Org. Chem., vol. 63, pp. 4545–4550 (1998).
Tetrahedron Letters, vol. 23, pp. 5299–5302 (1982).
"Compendium of Organic Methods", vol. 7, ed. March J., John Wiley & Sons, New York, pp. 353–357 (1992).

"Protective Groups in Organic Chemistry", Theodora W. Greene et al., John Wiley & Sons Inc., New York, pp. 309–348 (1991).

Schueller C.M. et al, Tetrahedron Letters NL, vol. 37, No. 49, pp. 8853–8856 (1996).

Vorwerk, S. et al, Angew. Chem., Int. Ed. (1998) 37 (12) pp. 1732–1734.

*Primary Examiner*—Paul J. Killos
(74) *Attorney, Agent, or Firm*—George W. Johnston; Dennis P. Tramaloni

(57) ABSTRACT

The invention provides a multistep synthesis for the preparation of 4,5-diamino shikimic acid derivatives of formula

I

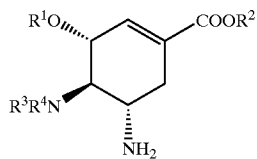

wherein $R^1$, $R^2$, $R^3$ and $R^4$ are defined in the specification, starting from furan. 4,5-Diamino shikimic acid derivatives are potent inhibitors of viral neuraminidase.

39 Claims, No Drawings

PROCESS FOR THE PREPARATION FOR 4, 5-DIAMINO SHIKIMIC ACID DERIVATIVES

FIELD OF THE INVENTION

The present invention relates to a multi-step process for the preparation of 4,5-diamino shikimic acid derivatives, especially for the preparation of (3R,4R,5S)-4-acetamido-5-amino-3-(1-ethylpropoxy)-1-cyclohexene-1-carboxylic acid ethyl ester and its pharmaceutically acceptable addition salts starting from furan as well as new specific intermediates.

BACKGROUND OF THE INVENTION 4,5-diamino shikimic acid derivatives, especially the (3R,4R,5S)-4-acetamido-5-amino-3-(1-ethylpropoxy)-1-cyclohexene-1-carboxylic acid ethyl ester and its pharmaceutically acceptable addition salts are potent inhibitors of viral neuraminidase( J. C. Rohloff et al., J.Org.Chem., 1998, 63, 4545–4550; WO 98/07685).

A multi step synthesis of (3R,4R,5S)-4-acetamido-5-amino-3-(1-ethylpropoxy)-1-cyclohexene-1-carboxylic acid ethyl ester from (−)-quinic acid or (−)-shikimic acid is described in (J. C. Rohloff et al, loc.cit.).

Both (−)-quinic acid and (−)-shikimic acid are starting compounds which are rather expensive and hardly accessible in technical quantities. A multi step synthesis capable to run on a technical scale should therefore preferably be based on starting compounds that are more attractive in price and available in technical quantities.

An object of the present invention therefore is to provide such a new access to the 4,5-diamino shikimic acid derivatives mentioned above in good yields and excellent quality.

SUMMARY OF THE INVENTION

It was found that the following synthesis could achieve this object.

The present invention therefore relates to a process for the preparation of a 4,5-diamino shikimic acid derivative of formula

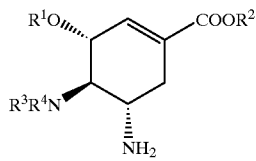

and pharmaceutically acceptable addition salts thereof wherein $R^1$ is an optionally substituted alkyl group, $R^2$ is an alkyl group and $R^3$ and $R^4$, independent of each other are H or an amino protecting group, with the proviso that not both $R^3$ and $R^4$ are H, a process which is characterized by steps a) through g), wherein step a)

furan is reacted with an acrylic acid derivative of the formula

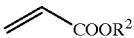

wherein $R^2$ is as above to form a bicyclo compound of formula

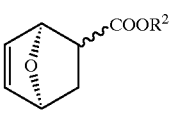

wherein $R^2$ is as above, step b)

the 2R-exo isomer of the bicyclo compound of formula (III) is separated, step c)

this 2R-exo isomer of the bicyclo compound of formula (III) is reacted with an azide to form an aziridine of formula

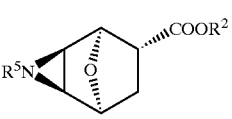

wherein $R^2$ is as above and wherein $R^5$ is the organic azide residue then, step d)

eliminative ring opening is effected to yield a cyclohexene aziridine derivative of formula

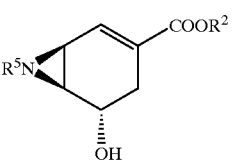

wherein $R^2$ and $R^5$ are as above, step e)

a substituent $R^6$ is introduced in the free OH-position and the aziridine ring is opened to give a cyclohexene derivative of formula

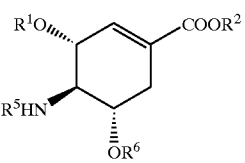

wherein $R^1$, $R^2$ and $R^5$ are as above and $R^6$ is a OH-protecting group, step f)

$R^5$ is removed to yield a 4-amino cyclohexene derivative of formula

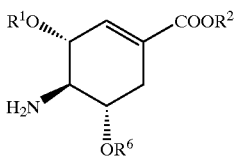

wherein $R^1$, $R^2$ and $R^6$ are as above
this 4-amino cyclohexene derivative of formula (VII) is finally processed to the 4,5-diamino shikimic acid derivatives of formula (I) by step g)
comprising either $g_{11}$ transformation of the 4-amino cyclohexene derivative of formula (VII) into an aziridine of formula

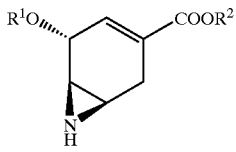

wherein $R^1$ and $R^2$ are as above,
$g_{12}$ formation of the azide of formula

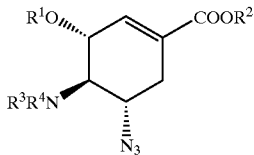

wherein $R^1$, $R^2$, $R^3$ and $R^4$ are as above and
$g_{13}$ reduction and, if necessary the formation of the pharmaceutically acceptable addition salt, or
$g_{21}$ transformation of the 4-amino cyclohexene derivative formula (VII)
into a 5-N-substituted-4,5-diamino shikimic acid derivative of formula

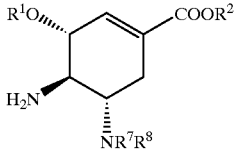

wherein $R^1$ and $R^2$ are as above and $R^7$ and $R^8$, independent of each other are H or an amino protecting group, with the proviso that not both $R^7$ and $R^8$ are H
$g_{22}$ acylation of the amino group in position 4 and
$g_{23}$ releasing the amino group in position 5 and, if necessary the formation of the pharmaceutically acceptable addition salt.

DETAILED DESCRIPTION OF THE INVENTION

The term alkyl in $R^1$ has the meaning of a straight chained or branched alkyl group of 1 to 20 C-atoms, expediently of 1 to 12 C-atoms. Examples of such alkyl groups are methyl, ethyl, n-propyl, i-propyl, n-butyl, i-butyl, tert.-butyl, pentyl and its isomers, hexyl and its somers, heptyl and its isomers, octyl and its isomers, nonyl and its isomers, decyl and its somers, undecyl and its isomers and dodecyl and its isomers.

This alkyl group can be substituted with one or more substituents as defined in e.g. WO 98/07685. Suitable substituents are alkyl of 1 to 20 C-atoms (as defined above), alkenyl with 2 to 20 C-atoms, cycloalkyl with 3 to 6 C-atoms, hydroxy, alkoxy with 1 to 20 C-atoms, alkoxycarbonyl with 1 to 20 C-atoms, F, Cl, Br, and I. Preferred meaning for $R^1$ is 1-ethylpropyl.

$R^2$ is a straight chained or branched alkyl group of 1 to 12 C-atoms, expediently of 1 to 6 C-atoms, as exemplified above.

Preferred meaning for $R^2$ is ethyl.

The substituent $R^6$ refers to any substituent for OH groups conventionally used and known in the art such as hydroxyl-protecting groups. They are described e.g. in "Compendium of Organic Methods" or in "Advanced Organic Chemistry", ed. March J., John Wiley & Sons, New York, 1992, 353–357.

Preferably $R^6$ is a sulfonyl group, more preferably optionally substituted aryl sulfonyl or alkyl sulfonyl such as p-toluenesulfonyl, p-nitrobenzenesulfonyl, p-bromo benzenesulfonyl, trifluoromethanesulfonyl or methanesulfonyl, most preferably methanesulfonyl.

The term amino protecting group in $R^3$ and $R^4$ or $R^7$ and $R^8$ refers to any substituent conventionally used and known in the art for protecting amino groups. They are described e.g. in "Protective Groups in Organic Chemistry", Theodora W. Greene et al., John Wiley &Sons Inc., New York, 1991, 315–385. Suitable substituents are also given in e.g. the WO 98/07685.

Preferred substituents for $R^3$ and $R^4$ are alkanoyl groups, more preferably lower alkanoyl with 1 to 6 C-atoms such as hexanoyl, pentanoyl, butanoyl (butyryl), propanoyl (propionyl), ethanoyl (acetyl) and methanoyl (formyl). Preferred alkanoyl group and therefore preferred meaning for $R^3$ is acetyl and for $R^4$ is H.

Preferred substituent for $R^7$ and $R^8$ is straight chained or branched alkenyl with 2 to 6 C-atoms, preferably allyl or an analog thereof. Suitable analog of allyl is an allyl group which is substituted on the $\alpha$-, $\beta$- or $\gamma$-carbon by one lower alkyl, lower alkenyl, lower alkynyl or aryl group. Suitable examples are e.g. 2-methylallyl, 3,3-dimethylallyl, 2-phenylallyl, or 3-methylallyl. Most preferred meaning for $R^7$ is allyl and for $R^8$ is H.

Preferred 4,5-diamino shikimic acid derivative of formula (I) is the (3R,4R,5S)-4-acetamido-5-amino-3-(1-ethylpropoxy)-1-cyclohexene-1-carboxylic acid ethyl ester and the ethyl (3R,4R,5S)-4-acetamido-5-amino-3-(1-ethylpropoxy)-1-cyclohexene-1-carboxylate Phosphate (1:1).

Step a)

Step a) comprises a Diels-Alder reaction of furan with an acrylic acid derivative. Diels-Alder reactions per se are known to the skilled in the art (see e.g. Tetrahedron Letters, 23, 1982, 5299–5302). The present conversion can therefore be performed following the methods and conditions described in the art.

Suitable derivatives of an acrylic acid are the esters and the amides, preferably the esters, more preferably lower alkyl esters of acrylic acid.

Usually this type of reaction needs the presence of Lewis acids. Suitable Lewis acids are magnesium halogenides such as magnesium chloride, magnesium bromide or magnesium iodide or zinc halogenides such as zinc chloride, zinc bromide or zinc iodide. Preferred Lewis acid was found to be zinc chloride.

As a rule catalytic amounts of the Lewis acid are applied, however it was surprisingly found that stoechiometric amounts or even an excess of the Lewis acid, preferably of zinc chloride within a reasonable time lead to an excellent exo/endo ratio of the bicyclo compound of formula (III) of up to 9:1.

Preferably stoichiometric amounts of zinc chloride are used.

Convenient solvent for step a) is the reactant acrylic acid derivative itself, used in an excess of up to 50%. It is however always possible to add an inert solvent.

The reaction temperature is not critical and can be chosen in the range of 20° C. to 70° C.

After termination of the reaction, recovery of the product can take place using methods well known to the skilled in the art.

Step b)

Step b) comprises separation of the 2R-exo isomer of the bicyclo compound of formula (III), preferably of the optical pure 2R-exo isomer of the bicyclo compound of formula (III).

Step a) provides the racemate of an exo/endo mixture of the bicyclo compound, wherein the exo form in the mixture is enriched up to a ratio of 9:1.

As a principle, separation of endo and exo forms of a compound can take place by taking advantage of the different physical properties of these forms such as different boiling points. Separation of each of the two optical isomers, however, has to take place either by classical racemate resolution techniques or by a stereoselective methods, e.g. by an enzymatic approach.

The desired 2R-exo form of the bicyclo compound can accordingly be isolated by physical separation of the exo and endo forms by any conventional technique which separates compounds according to their differing physical properties, e.g. by distillation, then separation of the 2R-exo and 2S-exo isomers by converting the exo-ester into the respective acid and finally by a subsequent racemate resolution using classical resolving agents such as (−)-ephedrin hydrochloride or S-(−)-1-phenyl ethylamine.

Preferably, however the exo/endo mixture of step a) is treated with an enzyme which is capable of specifically hydrolyzing the 2S-exo isomer and leaves the 2R-exo isomer unhydrolyzed. It was found that, ideally, lipases of the EC class 3.1.1.3 or lipoprotein lipases of the EC class 3.1.1.34 are used. Suitable representatives of these classes are lipases of the genus Candida, more preferably of *Candida antarctica*. Such lipases are commercially available. Most preferred enzyme is the B-form of lipase *Candida antarctica* which is offered under the tradename CHIRAZYME®L2 from Roche Diagnostics or as LIPASE SP-525 from Novo Nordisk.

As a common alternative immobilized enzymes may be used.

The reaction is usually carried out in an aqueous solution, preferably a monophasic or biphasic aqueous system, most preferably in a biphasic system with an apolar solvent as co-solvent. Suitable co-solvents are alkanes, cycloalkanes or cycloalkenes. Cyclohexane, cyclohexene and octane was found to be the most preferred co-solvent.

The common aqueous buffer solutions known to be used for biochemical conversions are used in order to maintain the pH in the range of 6.5 to 8.0. Suitably sodium or potassium phosphate buffers or borate buffers can be applied. Such a buffer solution can additionally contain NaCl or KCl in a concentration of 50 to 300 mM. A preferred buffering system could e.g. contain 0.1 M KCl and 5 mM potassium borate pH 7.5.

The ratio organic solvent/aqueous phase is in the range of 1:10 to 3:2. Overall substrate concentration is expediently chosen in the range of 5 to 20 wt. %, preferably in the range of 5 to 10 wt. %.

The reaction temperature is not critical. A suitable reaction temperature is 0° C. to 25° C., preferably close to freezing temperature of the reaction mixture.

The resulting 2S-exo acid is preferably neutralized by the controlled addition of a base such as NaOH or KOH, whereby the uncleaved 2R-exo ester together with the endo isomers remains in the organic phase and is separated by way of extraction with a common organic solvent.

Separation of the 2R-exo ester from the endo isomers can take place by a distillation in vacuo, preferably at a temperature in the range of 70° C. and 100° C. and a pressure of 0.1 mbar to 10 mbar.

Step c)

Step c) comprises the reaction of the 2R-exo isomer of the bicyclo compound of formula (III) with any azide, $R^5$—$N_3$, conventionally known or used in the art of organic synthesis. $R^5$ is any organic azide residue conventionally known or used in the art of organic synthesis.

Particularly suitable azides are found to be these which are capable to form an aziridine ring in endo-position to the bridgehead of the bicyclic system. Unexpectedly phosphoryl azides of the formula

$$R^{5'}N_3 \qquad\qquad XI$$

wherein $R^5$ is dialkoxyphosphoryl or diaryloxyphosphoryl, preferably diaryloxyphosphoryl, most preferably diphenyloxyphosphoryl fulfilled this task.

Most preferred phosphoryl azide is the diphenyloxyphosphoryl azide (DPPA).

The preference of DPPA is mainly based on its availability in technical quantities and its lower toxicity compared to the dialkoxyphosphoryl azides.

The phosphoryl azide is conveniently added in an amount of 0.8 equivalents to 1.0 equivalents relating to the 2R-exo bicyclo compound gained in step b). Preferably stoichiometric amounts of the phosphoryl azide are added.

The choice of a solvent is not critical as long as it is inert to the reactants. Toluene or dioxane were found to be suitable solvents.

The reaction temperature is not critical and can be chosen expediently between 40° C. and 80° C.

In case $R^5$ has the preferred meaning of diaryloxy phosphoryl, a transesterification can be performed to transform the diaryloxy phosphoryl group into a dialkoxy phosphoryl group.

Accordingly the organic azide residue $R^5$ is dialkoxy-phosphoryl, preferably di-($C_{1-6}$) alkoxy-phosphoryl, most preferably diethoxy-phosphoryl. Transesterifications are methods known to the skilled in the art, but as a rule take place in the presence of an alcoholate in the corresponding alcohol. Within the most preferred method transesterification takes place in the presence of sodium ethanolate in ethanol.

Step d)

Step d) comprises eliminative ring opening of the aziridine of formula (IV) to the cyclohexene aziridine derivative of formula (V).

This reaction is performed in the presence of a strong organic base. Expediently alkali-bis -(trialkylsilyl) amides, preferably alkali-bis-(trimethylsilyl) amides such as lithium bis-(trimethylsilyl) amide, sodium-bis-(trimethylsilyl) amide or potassium-bis-(trimethylsilyl) amide are used.

Usually the strong organic base is used in amount of 1.0 equivalent to 2.5 equivalents relating to one equivalent of the aziridine of formula (IV).

The choice of a solvent also for this step is not critical as long as it is inert to the reactants. Dioxane or tetrahydrofuran were found to be suitable solvents.

The reaction temperature is also not critical and may expediently be maintained in the range of −80° C. to 0° C., preferably in the range of −80° C. to −20° C.

The cyclohexene aziridine of formula (V) can be isolated after an acidic work up applying methods known to the skilled in the art.

Step e)

Step e) comprises introduction of a substituent $R^1$ in the free OH-position and ring opening of the aziridine ring to give cyclohexene derivatives of formula (VI).

The sequence of the reactions introducing substituent $R^6$ into the free OH-position and opening the ring is not critical. Preferably, substituent $R^6$ is introduced into the free OH-position first, followed by ring opening.

Compounds and methods for effecting such a substitution are well known in the art and described e.g. in "Compendium of Organic Methods" or in "Advanced Organic Chemistry", ed. March J., John Wiley & Sons, New York, 1992, 353–357.

It was found that the hydroxy group is preferably transformed into a sulfonic acid ester, $R^6$ therefore preferably is a sulfonyl group, more preferably optionally substituted aryl sulfonyl or alkyl sulfonyl such as p-toluenesulfonyl, p-nitrobenzenesulfonyl, p-bromo benzenesulfonyl, trifluoromethanesulfonyl or methanesulfonyl, most preferably methanesulfonyl.

Agents commonly used for producing sulfonic acid esters e.g. are the halogenides or the anhydrides of the following sulfonic acids: methanesulfonic acid, p-toluenesulfonic acid a p-nitrobenzenesulfonic acid, p-bromobenzenesulfonic acid or trifluoromethanesulfonic acid.

Preferred agent is a halogenide or anhydride of methanesulfonic acid such as methane sulfonylchloride.

The sulfonylating agent is expediently added in an amount of 1.0 to 1.2 equivalents relating to one equivalent of the cyclohexene aziridine of formula (V).

Although none of these variables are critical, usually the reaction takes place in an inert solvent such as in ethylacetate, at a reaction temperature of 0° C. to 20° C. and in the precence of an organic base.

For effecting the ring opening of the aziridine ring further the 0-substituted cyclohexane derivative of formula (V) is converted with an alcohol $R^1OH$, wherein $R^1$ is as above, in the presence of a Lewis acid. Following the preferences of $R^1$ given above most suitable alcohol is pentane-3-ol.

A suitable Lewis acid is e.g. bortrifluoride ethyl etherate which is usually added in an amount of 1.0 equivalent to 1.5 equivalents relating to one equivalent of the cyclohexene aziridine of formula (V).

Although none of these reactions are critical, the reaction expediently takes place in an inert solvent such as in a halogenated hydrocarbon like methylene chloride at temperatures between 0° C. and 40° C.

Alternatively the reaction can be performed without extra solvent thereby using the respective alcohol in sufficient excess.

Step f)

Step f) covers the removal of $R^5$ to yield the 4-amino cyclohexene derivative of formula (VII).

$R^5$ as outlined above preferably being dialkyl phosphoryl is advantageously splitted off using strong acidic conditions. Suitably a strong mineral acid such as sulfuric acid can be used. In order to achieve better crystallization the sulfate formed can be transformed with hydrochloric acid into the hydro chloride.

Although it is not critical to the reaction, the reaction conveniently takes place in a polar organic solvent such as in alcohols, preferably in alcohols which correspond to the ester residue $R^2$.

Step g)

As shown above step g) offers two different ways to come to the 4,5-diamino shikimic cid derivative of formula (I).

One way comprising the steps $g_{11}$ to $g_{13}$ passes an azide intermediate, whereby the other way comprising steps $g_{21}$ to $g_{23}$ follows an azide free route. Preferred route is the azide free route $g_{21}$ to $g_{23}$.

Steps $g_{11}$ to $g_{13}$.

Step $g_{11}$)

The transformation of the 4-amino cyclohexene derivative of formula (VII) to the aziridine of formula (VIII) can happen by reaction with a tertiary amine in the presence of an inert solvent.

Preferably triethylamine is selected as tertiary amine.

The tertiary amine is preferably applied in amounts of 2.0 equivalents to 2.5 equivalents relating to one equivalent of 4-amino cyclohexene derivative of formula (VII).

The choice of solvents is not critical. Good results have been achieved with ethylacetate or tetrahydrofuran.

Although not critical to the reaction, the reaction usually takes place at a temperature of 40° C. to 80° C.

steps $g_{12}$, $g_{13}$

These steps comprise the conversion of the aziridine of formula (VIII) to an azide and the subsequent reduction to the end product. These steps are known in the art and can be processed following the disclosure in scheme 5 of J. C. Rohloff et al., J.Org.Chem., 1998, 63, 4545–4550 and the corresponding experimental part thereof, which is incorporated herein by reference. Preferably, the aziridine ring of the compound of formula (VIII) is opened by reaction with an azide to form an azidoamine, followed by acylation of the amino group of the azidoamine with at least one aminoprotecting group to form the azide of formula (IX). The azide of formula (IX) is then reduced to form the 4,5-diamino shikimic acid of formula (I).

Steps $g_{21}$ to $g_{23}$ step $g_{21}$)

Step $g_{21}$) comprises the transformation of the 4-amino cyclohexene derivative of formula (VII) into a 5-N-substituted-4,5-diamino shikimic acid derivative of formula (X).

This transformation is expediently effected with an amine of formula $R^7NHR^8$, wherein $R^7$ and $R^8$ have the meaning as stated above. Preferred amines are allylamine, diallylamine or 2-methylallylamine whereby allylamine is the most preferred.

In order to release the amine the salt of the 4-amino cyclohexene derivative of formula (VII) as obtained in step f) is expediently neutralized first, either by addition of a common inorganic base such as sodium bicarbonate or by using the amine formula $R^7NHR^8$ in excess.

The reaction with the amine itself can be performed in an inert solvent, applying either normal or elevated pressure at temperatures of 20° C. to 150° C. As a suitable solvent tert.-butyl methyl ether can be selected.

Step g$_{22}$)

Step g$_{22}$) comprises the acylation of the free amino function of the 5-N-substituted 4,5-diamino shikimic acid derivative of formula (X).

Acylation can be effected under strong acidic conditions by using acylating agents known to the skilled in the art. Acylating agent can be an aliphatic or aromatic carboxylic acid, or an activated derivative thereof, such as an acyl halide, a carboxylic acid ester or a carboxylic acid anhydride. Suitable acylating agent preferably is an acetylating agent such as acetylchloride, trifluoracteylchloride or acetic anhydride. Suitable aromatic acylating agent is benzoylchloride. Strong acids suitably used e.g. are mixtures of methanesulfonic acid and acetic acid or sulfuric acid and acetic acid.

Acylation however can also take place under non acidic conditions using e.g. N-acetyl-imidazole or N-acetyl-N-methoxy-acetamide.

Preferably, however, the acylation takes place under acidic conditions using 0.5 to 2.0 equivalents of acetic anhydride, 0 to 15.0 equivalents of acetic acid and 0 to 2.0 equivalents of methanesulfonic acid in ethyl acetate.

An inert solvent such as tert.-butyl methyl ether maybe added, it is however also possible to run the reaction without addition of any solvent.

Although not critical to the reaction, the temperature is preferably chosen in the range of −20° C. to 100° C.

Step g$_{23}$)

Step g$_{23}$) comprises release of the amino group in position 5 and, if desired, further transformation of the resulting 4,5-diamino shikimic acid derivative of formula (I) into a pharmaceutically acceptable addition salt.

Release of the amino group is expediently effected by isomerization/hydrolysis in the presence of a suitable metal catalyst. Expediently a precious metal catalyst such as Pt, Pd or Rh either applied on an inert support such as charcoal or alumina, or in complexed form can be used. Preferred catalyst is 5 to 10% palladium on carbon (Pd/C).

The catalyst is suitably used in an amount of 2 to 30 wt. %, preferably, 5 to 20 wt. % relating to the 5-N-substituted 4,5-diamino shikimic acid derivative of formula (X).

The isomerization/hydrolysis is advantageously carried out in an aqueous solvent. The solvent itself can be protic or aprotic. Suitable protic solvents are e.g. alcohols such as methanol, ethanol or isopropanol. Suitable aprotic solvent is e.g. acetonitrile or dioxane.

The reaction temperature is not critical, but is preferably chosen in the range of 20° C. to 150° C.

It was found that isomerization/hydrolysis is preferably effected in the presence of a primary amine.

Primary amines suitably used are ethylenediamine or ethanolamine, or suitable derivatives thereof. A particularly preferred primary amine is ethanolamine.

The primary amine is suitably used in an amount of 1.0 to 1.25 equivalents, preferably of 1.05 to 1.15 equivalents relating to the 5-N-substituted 4,5-diamino shikimic acid derivative of formula (X).

In order to completely hydrolyze any imines that may have formed in this step, the reaction mixture is preferably treated with a mineral acid e.g. with sulfuric acid or hydrochloric acid.

Though the 4,5-diamino shikimic acid derivative can be isolated e.g. by evaporation and crystallization, it is preferably kept in e.g. an ethanolic solution and then further transformed into the pharmaceutically acceptable addition salt following the methods described in J. C. Rohloff et al., J.Org.Chem., 1998, 63; 4545–4550; WO 98/07685).

The term "pharmaceutically acceptable acid addition salts" embraces salts with inorganic and organic acids, such as hydrochloric acid, hydrobromic acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

The salt formation is effected in accordance with methods which are known per se and which are familiar to any person skilled in the art. Not only salts with inorganic acids, but also salts with organic acids come into consideration. Hydrochlorides, hydrobromides, sulfates, nitrates, citrates, acetates, maleates, succinates, methansulfonates, p-toluenesulfonates and the like are examples of such salts.

Preferred pharmaceutically acceptable acid addition salt is the 1:1 salt with phosphoric acid which can be formed preferably in ethanolic solution at a temperature of 50° C. to −20° C.

The invention further comprises a process for the preparation of the 2R-exo isomer of the bicyclo compound of formula

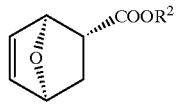

IIIa

This process is characterized by the treatment of the exo/endo mixture of the bicyclo compound of formula (III) as obtained from step a) with a lipase of the EC class 3. 1. 1. 3 or a lipoprotein lipase of the EC class 3. 1. 1. 34, the lipases thereby specifically hydrolyse the 2S-exo isomer and leaving the 2R-exo isomer untouched.

This specific process embodiment is identical to step b).

The respective description is incorporated herein by reference.

Accordingly, as stated under step b), preferred lipases are of the genus *Candida antarctica*.

The invention further comprises a process for the preparation of an aziridine of formula

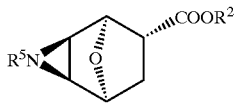

IV wherein $R^2$ is as above and wherein $R^5$ is the organic azide residue.

This process is characterized by the conversion of a 2R-exo isomer of the bicyclo compound of formula

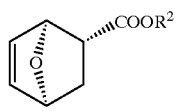

IIIa wherein $R^2$ is as above, with an azide.

This conversion is identical to step c) of the multistep synthesis described herein above. The respective description of step c) is incorporated herein by reference.

Preferred azide as stated above is diphenyloxyphosphoryl azide (DPPA).

The following key intermediates are new and not known to the state of the art they accordingly are an essential element of the present invention.

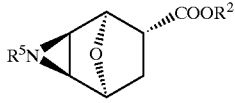

IV wherein $R^2$ is as above and wherein $R^5$ is the organic azide residue, preferably (1S,2S,4R,5R,6R)-3-(diethoxy-phosphoryl)-8-oxa-3-aza-tricyclo [3.2.1.0 2,4]octane-exo-6-carboxylic acid ethyl ester (with $R^2$=ethyl and $R^5$=diethoxy-phosphoryl) and (1S,2S,4R, 5R,6R)-3-(diphenyloxy-phosphoryl)-8-oxa-3-aza-tricyclo[3.2.1.0 2,4]octane-exo-6-carboxylic acid ethyl ester (with $R^2$=ethyl and $R^5$=diethoxy-phosphoryl).

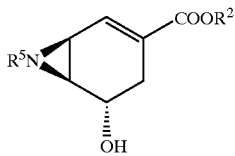

V wherein $R^2$ and $R^5$ are as above, preferably (1S,5S,6S)-7-(diethoxyphosphoryl)-5-hydroxy-7-aza-bicyclo [4.1.0]hept-2-ene-3-carboxylic acid ethyl ester (with $R^2$=ethyl and $R^1$=diethoxy-phosphoryl).

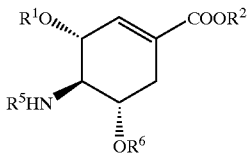

VI wherein $R^1$, $R^2$, $R^5$ and $R^6$ are as above and its pharmaceutically acceptable salts, preferably (3R,4S,5S)-4-(diethoxyphosphorylamino)-3-(1-ethyl-propoxy)-5-methanesulfonyloxy-cyclohex-1-ene carboxylic acid ethyl ester (with $R^1$=1-ethylpropyl, $R^2$=ethyl, $R^5$=diethoxy-phosphoryl and $R^6$=methanesulfonyl).

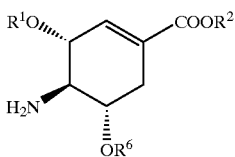

VII wherein $R^1$, $R^2$, $R^6$ are as above and its pharmaceutically acceptable salts, preferably (3R,4S,5S)-4-amino-3-(1-ethyl-propoxy)-5-methanesulfonyloxy-cyclohex-1-ene carboxylic acid ethyl ester hydrochloride (with $R^1$=1-ethylpropyl, $R^2$=ethyl, $R^6$=methanesulfonyl).

The following examples shall illustrate the invention in more detail without limiting it.

EXAMPLE 1

Preparation of 7-Oxa-bicyclo[2.2.1]hept-5-ene-2-carboxylic Acid Ethyl Ester (Endo/Exo Mixture)

A mixture of 300 g of furan (4.32 mol) and 611 g (6.05 mol) of ethyl acrylate was cooled to 3° C. in an ice bath under an inert atmosphere. 706 g (5.2 mol) of zinc chloride were added portionwise to the solution during 30 min, maintaining the temperature at between 10° C. and 20° C. After completed addition, the cooling bath was removed and the mixture was allowed to gradually heat up during 30 min to 50° C. by exothermy. It was subsequently kept at 50° C. during 27 h by means of an oil bath, then cooled to 40° C. and diluted with 200 ml of dichloromethane in order to reduce its viscosity. The solution was subsequently cooled to room temperature, poured on a mixture of 1.0 kg of crushed ice and 1.5 l of water and extracted. The aqueous phase was extracted with 2.5 l of ethyl acetate, and the combined organic phases were subsequently washed with 2.5 l of water, a solution of 109 g sodium bicarbonate in 2.5 l water, and 250 ml of brine. The organic phase was dried over sodium sulfate, filtered, evaporated at 45° C./1 mbar and dried at 40° C./0.06 mbar for 45 min, to yield 580 g (80%) of a 87:13 exo/endo mixture of product. Purity: 98% (HPLC; ISTD).

Data of exo-isomer: IR (film): 2984, 1734, 1448, 1370, 1343, 1315, 1277, 1217, 1098, 1047, 1019, 907, 874, 808, 722, 704 cm −1; MS (EI, 70 eV): 139, 123, 94, 81, 68, 55, 41, 39, 29 m/z.

Data of endo-isomer: IR (film): 2984, 1736, 1451, 1370, 1337, 1320,1304, 1194, 1131, 1095, 1055, 1025, 905, 855, 795, 712, 702 cm −1; MS (EI, 70 eV): 139, 123, 99, 95, 81, 68, 55, 43, 41, 39, 29 m/z.

EXAMPLE 2

Preparation of (1S,2R,4S)-7-Oxa-bicyclo[2.2.1]hept-5-ene-exo-2-carboxylic Acid Ethyl Ester 507.5 g (2.77 mol) of a 92:8 exo/endo-mixture of racemic 7-oxa-bicyclo[2.2.1]hept-5-ene-2-carboxylic acid ethyl ester was emulsified in 5.71 100 mM potassium chloride, 3 mM potassium phosphate buffer pH 7 and 3.7 l of octane ('Octane Fraction', Fluka 74830) by vigorous stirring. The emulsion was cooled to 1° C. and the pH adjusted to 7.5 with 1N NaOH solution. After addition of 0.75 MU of Chirazyme L-2 (Roche Diagnostics) the pH was maintained at 7.5 under vigorous stirring at 1° C. by the controlled addition (pH-stat) of 2.0 N NaOH-solution. After a total consumption of.930 ml 2.0 N NaOH-solution (corresponds to ca. 67% conversion with respect to the exo-isomer) after 10.6 h the reaction mixture was extracted with 3×8 l dichloromethane (the first time the emulsion was passed through a bed of 500 g dicalite filter aid in order to enhance phase separation; the solvent for the second extraction step was passed through the filter bed prior to use). The combined organic phases were dried on sodium sulfate, evaporated and dried on a high vacuum to give 160.5 g of a brownish oil. According to GC the title compound (93% ee) contained 20.5% of the endo-isomer, which was mostly removed from the mixture by distillation at 82° C.–86° C./3 mbar.

Data of exo-isorher: IR (film): 2984, 1734, 1448, 1370, 1343, 1315, 1277, 1217, 1098, 1047, 1019, 907, 874, 808, 722, 704 cm −1; MS (EI, 70 eV): 139, 123, 94, 81, 68, 55, 41, 39, 29 m/z.

EXAMPLE 3

Preparation of (1S,2S,4R,5R,6R)-3-(Diethoxyphosphoryl)-8-oxa-3-aza-tricyclo [3.2.1.0 2,4] octane-6-carboxylic Acid Ethyl Ester A solution of 32.3 g (192 mmol) of (1S,2R,4S)-7-oxa-bicyclo[2.2.1]hept-5-ene-exo-2-carboxylic acid ethyl ester and 48.4 g (167 mmol) diphenylphosphoryl azide in 32 ml of toluene was stirred at 70° C. for 18 h. Then 260 ml of ethanol were added, the mixture was cooled to 3° C. and 150 ml (403 mmol) of 21% sodium ethylate solution were added during 15 min, allowing the mixture to reach room temperature. The mixture was stirred for 30 min at room temperature, then poured on a solution of 650 g of crushed ice in 650 ml of brine. The aqueous phase was extracted twice with 650 ml of ethyl acetate, the combined organic phases were dried over sodium sulfate, filtered and evaporated to give 64.8 g of crude product, which was subsequently chromatographed over silica gel with a 9:1 mixture of ethyl acetate and dioxane as the eluent, yielding 32.5 g (53%) of the product as an oil. Purity: 99% (ISTD). $[\alpha]D_{20}$=+1.88 (c=1, EtOH).

IR (film): 3741, 2983, 2908, 1735, 1479, 1445, 1393, 1369, 1356, 1299, 1265, 1184, 1097, 1042, 983, 925, 897, 864, 833, 800, 740, 673 cm$^{-1}$; MS (EI, 70 eV): 320 (MH+), 290, 274, 262, 246, 234, 219, 191, 163, 109, 91, 81, 65, 55, 39 m/z.

Example 4

Preparation of (1S,5S,6S)-7-(Diethoxyphosphoryl)-5-hydroxy-7-aza-bicyclo[4.1.0]hept-2-ene-3-carboxylic Acid Ethyl Ester A solution of 64.1 g (197 mmol) of (1S,2S,4R,5R,6R)-3-(diethoxyphosphoryl)-8-oxa-3-aza-tricyclo [3.2.1.0 2,4] octane-6-carboxylic acid ethyl ester in 320 ml of THF was cooled to −65° C. Then 148 ml (296mmol) of 2 M sodium-bis-(trimethylsilyl)-amide in THF were added dropwise during 20 min, maintaining the temperature at below −60° C. The mixture was stirred at −60° C. for 5 h, then 1.20 l of ammonium chloride solution were added to the cold mixture, allowing it to reach 0° C. after completed addition. 110 ml of water were added to the suspension to give a clear solution, which was stirred for 30 min while reaching room temperature. The solution was extracted with 1.60 l of ethyl acetate, and the organic layer was washed with 60 ml of saturated sodium bicarbonate, dried over sodium sulfate, filtered and evaporated to give 57.1 g (91%) of product as an oil. Purity: 94% (ISTD). Optical rotation of further purified material: $[\alpha]D_{20}$=−37.7° (c=1, EtOH).

IR (film): 3381, 2983, 2910, 1712, 1647, 1446, 1393, 1258, 1213, 1165, 1136, 1096, 1028, 960, 932, 882, 848, 821, 801, 771, 748, 707, 655 cm$^{-1}$; MS (EI, 70eV): 319 (M+), 301, 290, 273, 262, 246, 234, 216, 202, 188, 174, 165, 137, 119, 109, 99, 91, 81, 65, 53, 45 m/e.

EXAMPLE 5

Preparation of (3R,4S,5S)-4-(Diethoxyphosphorylamino)-3-(1-ethyl-propoxy)-5-methanesulfonyloxy-cyclohex-1-enecarboxylic Acid Ethyl Ester A solution of 25.13 g (78.7 mmol) of (1S,5S,6S)-7-(diethoxyphosphoryl)-5-hydroxy-7-aza-bicyclo[4.1.0]hept-2-ene-3-carboxylic acid ethyl ester and 9.61 g (94.4 mmol) of triethylamine in 250 ml of ethyl acetate was cooled to 0° C. 10.0 g (94.4 mmol) of methanesulfonic acid chloride were added dropwise during 10 min, maintaining the temperature below 10° C. After completed addition, the mixture was allowed to reach room temperature during 20 min, and the triethylamine hydro-chloride precipitate was filtered off and washed in several portions with a total of 75 ml of ethyl acetate. The combined filtrates were evaporated to give 35.1 g of a brownish oil, which was sub-sequently dissolved in 75 ml of dichloromethane. 220 ml (2.03 mol) of 3-pentanol were added, the mixture was cooled to 0° C., and 14.8 ml (118 mmol) of BF3*OEt$_2$ were added during 10 min, maintaining the temperature at below 4° C. After completed addition, the mixture was stirred for 1.5 h at room temperature. The crude reaction mixture was evaporated at 30° C. (removal of excess of 3-pentanol), and the resulting oil was partitioned between 500 ml of ethyl acetate and 250 ml of saturated sodium bicarbonate solution. The organic layer was washed with 20 ml of brine, dried over sodium sulfate, filtered and evaporated to give 36.4 g of a brownish solid.

Purification: 36.3 g of above crude product was taken up in 240 ml of ethyl acetate and heated to 60° C. to give a clear solution. The solution was allowed to gradually cool to room temperature during 2 h, being seeded with product crystals at 50° C. The resulting suspension was stirred for 1 h at room temperature, filtered, washed portionwise with a total of 35 ml of ethyl acetate, and dried at 45° C./5 mbar for 30 min to give a first portion of 15.67 g product as white crystals. The combined mother liquor and washings were evaporated, taken up in a mixture 50 ml of ethyl acetate and 25 ml of n-heptane and heated to 70° C. The mixture was allowed to cool to room temperature during 1.5 h, being seeded with product crystals at 50° C. The suspension was stirred for 15 min at room temperature and filtered. The residue was washed with a mixture of 7.5 ml of ethyl acetate and 2.5 ml of n-heptane and dried at 45° C./5 mbar for 45 min to give a second portion of 8.28 g product as white crystals. Both product portions were combined to give 23.95 g (63%) product, m.p. 140.5 –141.0° C. Purity: 95% (ISTD). Optical rotation of further purified material: $[\alpha]D_{20}$=−26.5° (c=1, EtOH).

IR (film): 3210, 2925,2854, 1720, 1663, 1466, 1351, 1286, 1252, 1221, 1175, 1156, 1142, 1107, 1070, 1040, 966, 915, 895, 838, 811, 782, 748, 732 cm$^{-1}$; MS (EI, 70 eV): 486 (M+), 416, 398, 320, 302,286, 274,246 m/e.

EXAMPLE 6

Preparation of (3R,4S,5S)-4-amino-3-(1-ethyl-propoxy)-5-methanesulfonyloxy-cyclohex-1-enecarboxylic Acid Ethyl Eester Hydrochloride A solution of 22.07 g (41.4 mmol) of (3R,4S,5S)-4-(diethoxyphosphorylamino)-3-(1-ethyl-propoxy)-5-methanesulfonyloxy-cyclohex-1-enecarboxylic acid ethyl ester in 90 ml of ethanol was cooled to 0° C. 22 ml (395 mmol) of 96% sulfuric acid were added dropwise during 25 min, maintaining the temperature at below 20° C. After completed addition, the mixture was stirred for 22 h at 70° C., then cooled to 0° and poured on an ice cold mixture of 1.0 l of ethyl acetate and 1.0 l of 10% (w/v) sodium hydroxide solution. After extraction, the phases were separated and the organic phase was washed with 280 ml of water, dried over sodium sulfate, filtered and evaporated to give 14.9 g of crude product. This material was taken up in 90 ml of tert.-butyl methyl ester, the suspension heated to 50° C. to give a clear, brownish solution, and cooled to 10° C., where 30 ml of 4M HCl in ethanol were added, maintaining the temperature at below 20° C. After about 1 minute the product started to precipitate. The thick suspension was diluted with 50 ml of n-hexane and stirred for 15 min at room temperature. The precipitate was filtered off and dried at 40° C./3 mbar for 30 min to give 11.09 g ( 63%) of product as white crystals.

IR (film): 3233, 2923, 2853, 2687, 2579, 1989, 1717, 1654, 1586, 1487, 1464, 1357, 1340, 1266, 1225, 1177, 1067, 1021, 973, 940, 906, 885, 830, 747, 729 cm$^{-1}$.

EXAMPLE 7

Preparation of (3R,4R,5S) -5-Allylamino-4-amino-3-(1-ethyl-propoxy)-cyclohex-1-enecarboxylic Acid Ethyl Ester A solution of 6.95 g (19.9 mmol) of (3R,4S,5S)-4-amino-3-(1-ethyl-propoxy)-5-methanesulfonyloxy-cyclohex-1-enecarboxylic acid ethyl ester hydrochloride and 6.1 ml (79.6 mmol) of allylamine in 82 ml of tert.-butyl methyl ester was sealed in a pressure vessel under argon and heated to 110° C., resulting in a 4 bar internal pressure. After 20 h the mixture was cooled to room temperature and partitioned between 30 ml of tert.-butyl methyl ester and 120 ml of saturated sodium bicarbonate solution. The aqueous phase was extracted with 50 ml tert.-butyl methyl ester, and the combined organic phases were dried over sodium sulfate, filtered and evaporated to give 5.90 g (96%) of product as a slightly brownish oil. Purity: 77% (ISTD).

IR(film): 3274, 3084, 2925, 2853, 1721, 1645, 1556, 1457, 1373, 1318, 1249, 1185, 1130, 1087, 1057, 1037, 995, 938, 770, 736; MS (70 eV): 353 (M+), 296, 283, 265, 226 m/e.

EXAMPLE 8

Preparation of (3R,4R,5S)-4-acetylamino-5-Allylamino-3-(1-ethyl-propoxy)-cyclohex-1-enecarboxylic Acid Ethyl Ester In a 4l4-necked round bottom flask equipped with a thermometer, a mechanical stirrer, a Claisen condenser and an inert gas supply 278.0 g of (3R,4R,5S)-5-allylamino-4-amino-3-(1-ethyl-propoxy)-cyclohex-1-enecarboxylic acid ethyl ester obtained according to (c) were dissolved at room temperature with stirring under argon in 2800 ml of tert.-butyl methyl ether. From the red solution 1400 ml of tert.-butyl methyl ether were distilled. Again 1400 ml of tert.-butyl methyl ether were added and distilled off. The red solution was cooled to 0–5° C. and treated with 512 ml of acetic acid (9.0 mol) whereby the temperature rose to about 23° C. After cooling to 0° C.–5° C. 58.1 ml of methanesulfonic acid (d=1.482, 0.90 mol) were added dropwise in the course of 27 min followed by 84.7 ml of acetic anhydride (d=1.08, 0.90 mol) added dropwise in the course of 40 min keeping the temperature in the range of 0° C. to 5° C. The brown reaction mixture was stirred without cooling for 14 h then treated with vigorous stirring with 1400 ml of water (deionized) for 30 min and the brown organic phase was extracted with 450 ml of IM aqueous methanesulfonic acid. The combined aqueous phases (pH=1.6) were treated with stirring with about 694 ml of 50% aqueous potassium hydroxide until pH=10.0 was reached, keeping the temperature in the range of 10 to 25° C. The brown, turbid mixture was extracted first with 1000 ml then with 400 ml, in total with 1400 ml of tert.-butyl methyl ether, the combined organic extracts were stirred over 32 g of charcoal and filtered. The filter cake was washed with about 200 ml tert.-butyl methyl ether and the combined filtrates were evaporated in a rotary evaporator at 47° C./380 to 10 mbar to yield 285.4 g of brown-red, amorphous crystals which were dissolved with stirring in a mixture of 570 ml of tert.-butyl methyl ether and 285 ml of n-hexane at 50° C. The brown solution was cooled in 45 min with stirring to −20° C. to −25° C. and stirred for 5 h whereby brown crystals precipitated. The suspension was filtered over a pre-cooled (−20° C.) glass filter funnel and the filter cake was washed with a pre-cooled (−20° C.) mixture of 285 ml of tert.-butyl methyl ether and 143 ml of n-hexane and dried in a rotary evaporator at 48° C.<10 mbar to yield 200.33 g (83%) of (3R,4R,5S)-4-acetylamino-5-allylamino-3-(1-ethyl-propoxy)-cyclohex-1-enecarboxylic acid ethyl ester; m.p. 100.2° C.–104.2° C.

EXAMPLE 9

Preparation of (3R,4R,5S)-4-acetylamino-5-amino-3-(1-ethyl-propoxy)-cyclohex-1-enecarboxylic Acid Ethyl Ester In a 1l4-necked round bottom flask equipped with a thermometer, a mechanical stirrer, a reflux condenser and an inert gas supply 176.2 g of (3R,4R,5S)-4-acetylamino-5-allylamino-3-(1-ethyl-propoxy)-cyclohex-1-enecarboxylic acid ethyl ester obtained according to example 8 and 30.0 ml of ethanolamine. (d=1.015, 0.54 mol) were dissolved at room temperature in 880 ml of ethanol and treated with 17.6 g of 10% palladium on charcoal. The black suspension was heated to reflux for 3 h, cooled to room temperature and filtered. The filter cake was washed with 100 ml of ethanol and the combined filtrates were evaporated in a rotary evaporator at 50° C./<20 mbar. The brown, oily residue (207.3 g) was treated with 600 ml of 2N hydrochloric acid and the brown solution was distilled in a rotary evaporator at 50° C./75 mbar for 5 min. The solution was cooled to room temperature, washed with 600 ml of tert.-butyl methyl ether and treated with stirring and cooling with about 110 ml of 25% aqueous ammonia keeping the temperature below room temperature until pH=9–10 was reached and a brown emulsion formed. The emulsion was extracted three times with 600 ml, in total with 1800 ml of ethyl acetate. The combined extracts were dried over about 200 g of sodium sulfate and filtered. The filter cake was washed with about 200 ml of ethyl acetate and the combined filtrates were evaporated in a rotary evaporator at 50° C./<20 mbar to yield 158.6 g of a brown oil which was dissolved in 650 ml ethanol. The brown solution was added in the course of 1 min with stirring to a hot solution (50° C) of 57.60 g of 85% ortho-phosphoric acid (d=1.71, 0.50 mol) in 2500 ml of ethanol. The resulting solution was cooled in the course of 1 h to 22° C. At 40° C. seed crystals of (3R,4R,5S)-4-acetylamino-5-amino-3-(1-ethyl-propoxy)-cyclohex-1-enecarboxylic acid ethyl ester (about 10 mg) were added whereby crystallization started. The beige suspension was cooled in the course of 2 h to −20° C. to −25° C. and stirred at this temperature for 5 h. The suspension was filtered over a pre-cooled (−20° C.) glass filter funnel for 2 h. The filter cake was first washed with 200 ml of ethanol pre-cooled to −25° C., then twice with 850 ml, in total with 1700 ml acetone, then twice with 1000 ml, in total with 2000 ml of n-hexane, then dried at 50° C./20 mbar for 3 h to yield 124.9 g (70%) of (3R,4R,5S)-4-acetylamino-5-amino-3-(1-ethyl-propoxy)-cyclohex-1-ene carboxylic acid ethyl ester as white crystals; m.p. 205–207° C., decomposition.

We claim:

1. A process for the preparation of a 4,5-diamino shikimic acid derivative of formula

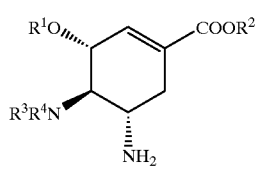

I and pharmaceutically acceptable addition salts thereof wherein $R^1$ is an alkyl group of 1 to 20 carbon atoms, $R^2$ is an alkyl group of 1 to 12 carbon atoms, $R^3$ is an amino-protecting group and
$R^4$ is H or an amino-protecting group;
the process comprising steps a), b), c), d), e), f), $g_{11}$), $g_{12}$) and $g_{,13}$):

step a)
  reacting, by a Diels-Alder reaction, furan with an acrylic acid derivative of the formula

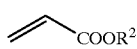

II wherein $R^2$ is as above
to form a mixture of a 2R-exo isomer and other stereoisomers of a bicyclo compound of formula

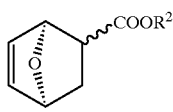

III wherein $R^2$ is as above;

step b)
  isolating the 2R-exo isomer of the bicyclo compound of formula (III) from the mixture of 2R-exo isomer and other stereoisomers of the bicyclo compound of formula (III);

step c)
  reacting the isolated 2R-exo isomer of the bicyclo compound of formula (III) with an organic azide $R^5$-$N_3$ in an inert solvent to form an aziridine of formula

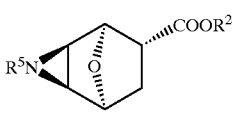

IV wherein $R^2$ is as above and $R^5$ is a residue of the organic azide;

step d)
  reacting the aziridine of formula (IV) in the presence of an organic base to yield a cyclohexene aziridine derivative of formula

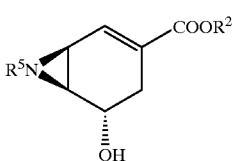

V wherein $R^2$ and $R^5$ are as above;

step e)
  introducing an OH-protecting group $R^6$ in the free OH-position of the cyclohexene aziridine derivative of formula (V) and reacting the aziridine ring of the cyclohexene aziridine derivative of formula (V) with $R^1$OH to form a cyclohexene derivative of formula

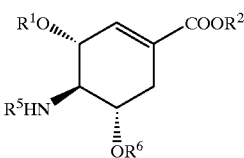

VI wherein $R^1$, $R^2$ and $R^5$ are as above and $R^6$ is an OH-protecting group;

step f)
  removing $R^5$ from the cyclohexene derivative of formula (VI) to yield a 4-amino cyclohexene derivative of formula

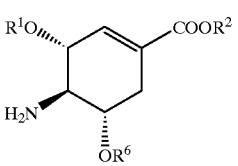

VII wherein $R^1$, $R^2$ and $R^6$ are as above;

step $g_{11}$)
  reacting the 4-amino cyclohexene derivative of formula (VII) with a tertiary amine to form an aziridine of formula

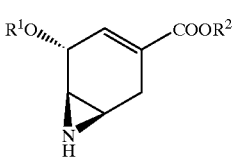

VIII wherein $R^1$ and $R^2$ are as above;

step $g_{12}$)
  converting the aziridine of formula (VIII) to an azide of formula

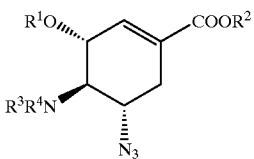

IX wherein $R^1$, $R^2$, $R^3$ and $R^4$ are as above
by aziridine ring opening by reaction with an azide to form an azidoamine, followed by acylation of the azidoamine with at least one amino-protecting group; and step $g_{13}$)
  reducing the azide of formula (IX) to form the 4,5-diamino shikimic acid derivative of formula (I).

2. The process of claim 1, wherein the reaction of furan with the acrylic acid derivative of formula (II) in step a) is performed in the presence of a Lewis acid.

3. The process of claim 2 wherein the Lewis acid is zinc chloride used in stoichiometric amounts relating to the bicyclo compound of formula (III).

4. The process of claim 1, wherein the OH-protecting group $R^6$ is a sulfonic acid ester.

5. The process of claim 4, wherein the OH-protecting group $R^6$ is methanesulfonic acid ester.

6. The process of claim 1, wherein the removal of $R^5$ in step f) takes place under strong acidic conditions.

7. A process for the preparation of a 4,5-diamino shikimic acid derivative of formula

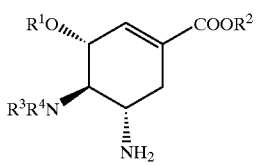

I and pharmaceutically acceptable addition salts thereof wherein $R^1$ is an alkyl group of 1 to 20 carbon atoms, $R^2$ is an alkyl group of 1 to 12 carbon atoms, $R^3$ is an amino-protecting group and $R^4$ is H or an amino-protecting group;

the process comprising steps a), b), c), d), e), f), $g_{21}$), $g_{22}$) and $g_{23}$):

step a)
reacting furan with an acrylic acid derivative of the formula

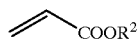

II wherein $R^2$ is as above to form a mixture of a 2R-exo isomer and other stereoisomers of a bicyclo compound of formula

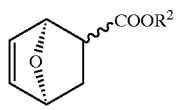

III wherein $R^2$ is as above;

step b)
isolating the 2R-exo isomer of the bicyclo compound of formula (III) from the mixture of 2R-exo isomer and other stereoisomers of the bicyclo compound of formula (III);

step c)
reacting the isolated 2R-exo isomer of the bicyclo compound of formula (III) with an organic azide $R^5$-$N_3$ to form an aziridine of formula

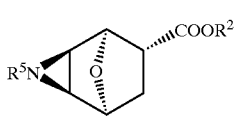

IV wherein $R^2$ is as above and $R^5$ is a organic azide residue;

step d)
reacting the aziridine of formula (IV) in the presence of an organic base to yield a cyclohexene aziridine derivative of formula

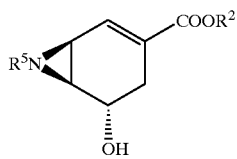

V wherein $R^2$ and $R^5$ are as above;

step e)
introducing an OH-protecting group $R^6$ in the free OH-position of the cyclohexene aziridine derivative of formula (V) and reacting the aziridine ring of the cyclohexene aziridine derivative of formula (V) with $R^1OH$ to form a cyclohexene derivative of formula

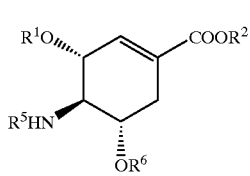

VI wherein $R^1$, $R^2$ and $R^5$ are as above and $R^6$ is an OH-protecting group;

step f)
removing $R^5$ from the cyclohexene derivative of formula (VI) to yield a 4-amino cyclohexene derivative of formula

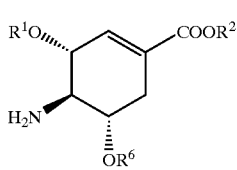

VII wherein $R^1$, $R^2$ and $R^6$ are as above;

step $g_{21}$)
reacting the 4-amino cyclohexene derivative of formula (VII) with $R^7NHR^8$ to form a 5-N-substituted-4,5-diamino shikimic acid derivative of formula

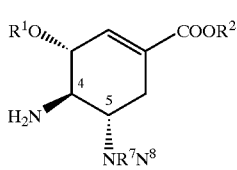

X wherein $R^1$ and $R^2$ are as above, $R^7$ is an amino-protecting group and $R^8$ is H or an amino-protecting group;

step $g_{22}$)
substituting an amino-protecting group for one or both of the hydrogens of the amino group in position 4 of the 5-N-substituted-4,5-diamino shikimic acid derivative of formula (X) to form a substituted product; and step g$_{23}$)
removing the amino-protecting groups in position 5 of the substituted product of step g$_{22}$) to form the 4,5-diamino shikimic acid derivative of formula (I).

8. The process of claim 7, wherein the reaction of furan with the acrylic acid derivative of formula (II) in step a) is performed in the presence of a Lewis acid.

9. The process of claim 8 wherein the Lewis acid is zinc chloride used in stoichiometric amounts relating to the bicyclo compound of formula (III).

10. The process of claim 7, wherein the OH-protecting group R$^6$ is a sulfonic acid ester.

11. The process of claim 10, wherein the OH-protecting group R$^6$ is methanesulfonic acid ester.

12. The process of claim 7, wherein the removal of R$^5$ in step f) takes place under strong acidic conditions.

13. A process for the isolation of a 2R-exo isomer of the bicyclo compound of formula

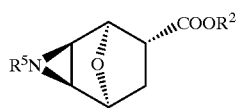

IIIa from a mixture of the 2R-exo isomer and other stereoisomers of the bicyclo compound of formula (III)

III the process comprising treating the mixture of the 2R-exo isomer and other stereoisomers of the bicyclo compound of formula (III) in an aqueous solution with an enzyme selected from the group consisting of lipases of the EC class 3. 1. 1. 3 and lipoprotein lipases of the EC class 3. 1. 1. 34 to specifically hydrolyze any 2S-exo isomers present in the mixture, followed by separation of the 2-exo isomer of formula (IIIA) from any endo isomers of formula (III).

14. The process of claim 13, wherein the enzyme is a lipase of the genus *Candida antarctica*.

15. The process of claim 13, wherein the aqueous solution has a pH of from about 6.5 to about 8.0.

16. A process for the preparation of an aziridine of formula

IV wherein R$^2$ is an alkyl group of 1 to 12 carbon atoms and R$^5$ is an organic azide residue, comprising
reacting a 2R-exo isomer of the bicyclo compound of formula

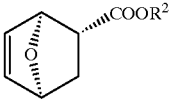

IIIa wherein R$^2$ is as above with an organic azide R$^5$-N$_3$ in an inert solvent.

17. The process of claim 16 wherein the organic azide R$^5$-N$_3$ is a phosphoryl azide.

18. The process of claim 17, wherein the organic azide R$^5$-N$_3$ is a dialkoxyphosphoryl azide or a diaryloxyphosphoryl azide.

19. The process of claim 17, wherein the organic azide R$^5$-N$_3$ is a diphenyloxy-phosphoryl azide.

20. A compound of the formula

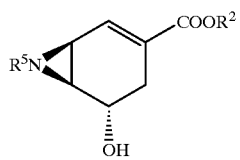

IV wherein R$^2$ is an alkyl group having 1 to 12 carbon atoms and R$^5$ is an organic azide residue.

21. The compound of claim 20, wherein R$^5$ is a phosphoryl group.

22. The compound of claim 21, wherein R$^5$ is a dialkoxyphosphoryl group or a diaryloxyphosphoryl group.

23. The compound of claim 22, wherein R$^5$ is diphenyloxy-phosphoryl.

24. The compound of claim 22, comprising (1S,2S,4R, 5R,6R)-3-(diethoxy-phosphoryl)-8-oxa-3-aza-tricyclo [3.2.1.0 2,4]octane-exo-6-carboxylic acid ethyl ester.

25. The compound of claim 22, comprising (1S,2S,4R, 5R,6R)-3-(diphenyloxy-phosphoryl)-8-oxa-3-aza-tricyclo [3.2.1.0 2,4]octane-exo-6-carboxylic acid ethyl ester.

26. A compound of the formula

V wherein R$^2$ is an alkyl group of 1 to 12 carbon atoms and R$^5$ is an organic azide residue.

27. The compound of claim 26, wherein R$^5$ is a phosphoryl group.

28. The compound of claim 27, wherein R$^5$ is a dialkoxyphosphoryl group or a diaryloxyphosphoryl group.

29. The compound of claim 28, wherein R$^5$ is diphenyloxy-phosphoryl.

30. The compound of claim 28, comprising (1S,5S,6S)-7-(diethoxyphosphoryl)-5-hydroxy-7-aza-bicyclo[4.1.0] hept-2-ene-3-carboxylic acid ethyl ester.

31. A compound of the formula

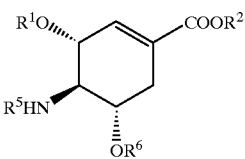

VI wherein $R^1$ is an alkyl group having 1 to 20 carbon atoms, $R^2$ is an alkyl group having 1 to 12 carbon atoms, $R^5$ is an organic azide residue and $R^6$ is an OH-protecting group.

32. The compound of claim 31, wherein $R^1$ is a substituted alkyl group having 1 to 20 carbon atoms.

33. The compound of claim 31, wherein $R^5$ is a phosphoryl group.

34. The compound of claim 33, wherein $R^5$ is a dialkoxyphosphoryl group or a diaryloxyphosphoryl group.

35. The compound of claim 34, wherein $R^5$ is diphenyloxy-phosphoryl.

36. The compound of claim 34, comprising (3R,4S,5S)-4-(diethoxyphosphorylamino)-3-(1-ethyl-propoxy)-5-methanesulfonyloxy-cyclohex-1-ene carboxylic acid ethyl ester.

37. A compound of the formula

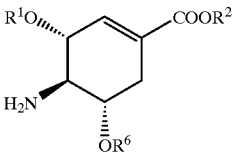

VII wherein $R^1$ is an alkyl group having 1 to 20 carbon atoms, $R^2$ is an alkyl group having 1 to 12 carbon atoms and $R^6$ is a OH-protecting group.

38. The compound of claim 37, wherein $R^1$ is a substituted alkyl group having 1 to 20 carbon atoms.

39. The compound of claim 37, comprising (3R,4S,5S)-4-amino-3-(1-ethyl-propoxy)-5-methanesulfonyloxy-cyclohex-1-enecarboxylic acid ethyl ester hydrochloride.

* * * * *

UNITED STATES PATENT AND TRADEMARK OFFICE
CERTIFICATE OF CORRECTION

PATENT NO.    : 6,403,824 B2
DATED         : June 11, 2002
INVENTOR(S)   : Stefan Abrecht et al.

It is certified that error appears in the above-identified patent and that said Letters Patent is hereby corrected as shown below:

<u>Title page,</u>
Please insert the following:

-- [30] Foreign Application Priority Data
    February 22, 2000    (EP)    00103673.0 --

Signed and Sealed this

Fifth Day of November, 2002

Attest:

Attesting Officer

JAMES E. ROGAN
*Director of the United States Patent and Trademark Office*